United States Patent [19]

Hydén et al.

[11] 4,061,141
[45] Dec. 6, 1977

[54] APPARATUS AND METHOD FOR SELECTIVELY SEPARATING AMINO ACIDS AND DEFINED PROTEINS IN BLOOD

[76] Inventors: Viktor Holger Hydén, Prastgardsgaten 2; Fritz Victor Hasselblad, St. Eriks Torg 3, both of Goteborg, Sweden

[21] Appl. No.: 223,577

[22] Filed: Feb. 4, 1972

Related U.S. Application Data

[63] Continuation-in-part of Ser. No. 850,576, Aug. 15, 1969, abandoned.

[30] Foreign Application Priority Data

Mar. 21, 1969 Sweden ........................ 4029/69

[51] Int. Cl.² .................................................. A61M 1/03
[52] U.S. Cl. .......................... 128/214 R; 23/258.5 R; 128/DIG. 3; 195/66 A
[58] Field of Search ............. 128/213, 214 R, 334 R, 128/DIG. 3; 3/1; 23/258.5; 210/22, 23, 321; 195/1.7, 1.8, 127, 66, DIG. 11; 424/101, 94

[56] References Cited

U.S. PATENT DOCUMENTS

| | | | |
|---|---|---|---|
| 3,608,729 | 9/1971 | Haselden | 210/321 |
| 3,617,545 | 11/1971 | Dubois | 210/22 |
| 3,619,423 | 11/1971 | Galletti et al. | 210/321 X |
| 3,669,878 | 6/1972 | Marantz | 210/22 |

FOREIGN PATENT DOCUMENTS

| | | | |
|---|---|---|---|
| 320,155 | 2/1970 | Sweden | 128/214 R |
| 953,414 | 3/1964 | United Kingdom | 128/214 R |

OTHER PUBLICATIONS

Brown et al. — Cancer Research — vol. 30, Nov. 1970, pp. 2736-2738.
Hill et al. — Jama, Nov. 27, 1967, vol. 202, No. 9, pp. 882-888.
Rubin et al. — Trans. Amer. Soc. Art. Int. Orgs., vol. XIV, 1968, pp. 169-174.
Chang—Trans. Amer. Soc. Artif. Inter. Orgs., 1968, vol. XIV, pp. 163-168.

*Primary Examiner*—Dalton L. Truluck
*Attorney, Agent, or Firm*—Toren, McGeady and Stanger

[57] ABSTRACT

There is provided an apparatus and method for selectively separating amino acids and defined proteins from the blood by enzymatic degradation, to obtain a therapeutic effect. The apparatus includes a closed system in which is mounted a membrane like structure presenting a wide surface area on which has been fixed the enzyme or enzymes necessary to effect the separation process together with heparin to render the surface non-thrombogenous. The method of selectively separating the amino acids and proteins resides in causing blood to pass from an artery in the patient over the active surface containing the enzyme and heparin and returning the blood to the patient via another blood vessel.

18 Claims, 11 Drawing Figures

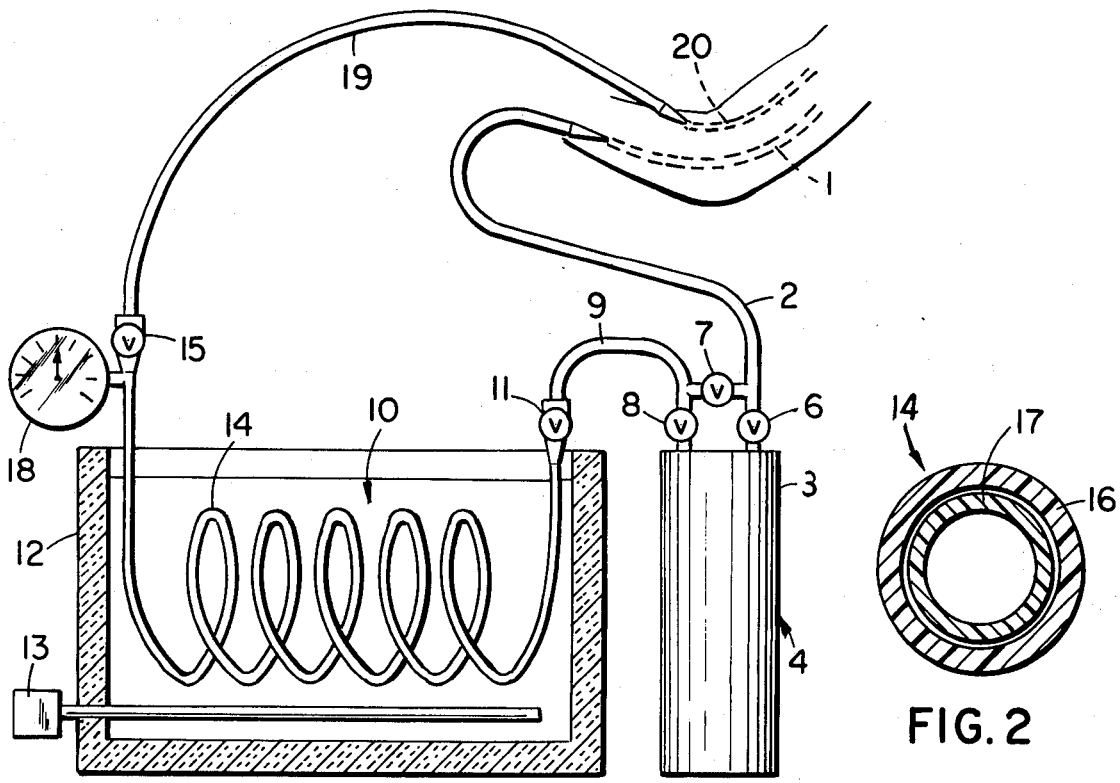
FIG. 1
FIG. 2
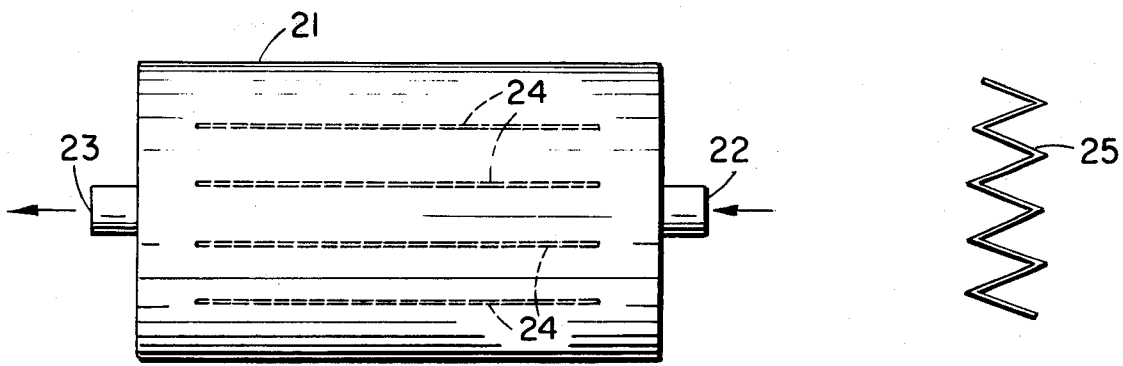
FIG. 3
FIG. 4

APPARATUS AND METHOD FOR SELECTIVELY SEPARATING AMINO ACIDS AND DEFINED PROTEINS IN BLOOD

This is a continuation-in-part application of Ser. No. 850,576 filed Aug. 15, 1969 now abandoned.

SUMMARY OF THE INVENTION

The present invention relates generally to the use of enzymes for separating components contained in the blood and, more particularly, it is directed to an apparatus and method for selectively separating by enzymatic degradation amino acids and defined proteins in the blood for a period of time sufficient to achieve a therapeutic effect. Such therapy is desirable when treating tumours, the growth of which requires normal concentration in the blood of one specific amino acid or of several amino acids, as in genetically conditioned metabolic diseases, such as phenylketoneuria. Transamination of alanine and glutamic acid or oxidative deamination by amino acid oxydases are examples of selective separation as meant here; while an example of relevant proteins includes acidic, soluble proteins rich in glutaminic acid and having a molecular weight of from 4000-30000.

It has hitherto been impossible in practice to separate selectively amino acids and defined proteins for therapeutic purposes from human blood and the blood of animals.

Concerning the use of enzymes in removing components from blood reference is made to "Microcopoules as Artifidal Cells", T. M. S. Chang, Science Journal, July 1967, pp 62-67.

It is known that the enzymes necessary for the selective separation process, such enzymes being both expensive and difficult to prepare, have a very limited active life when present in a free state in solution, but that they become stabilized and retain their activity for considerably longer periods if fixed to the surface of an appropriate carrier substance. There are two known types of such substances; namely collagen, which when prepared with formaldehyde and phenol for instance is made sufficiently resistant and suitable for the purpose in question, and polymers an copolymers such as polyacrylonitrile.

The enzyme in question is coupled in a known manner to these two substances. Similarly, heparin is coupld to the carrier substance by ionic bonds, to render the substance nonthrombogenous.

Enzymes capable of being insolubilized on the carrier substance and which are of value in affecting the liquid or cellular phase of blood include a wide variety of enzymes. Such enzymes can be classified under three general headings: (1) hydrolytic enzymes, (2) redox enzymes and (3) transferase enzymes.

The first group, hydrolytic enzymes, include proteolytic enzymes which hydrolyze proteins, e.g. pepsin, trypsin, chymotrypsin; carbohydrases which hydrolyze carbohydrates; esterases which hydrolyze esters, e.g. lipase, cholinesterase, lecithinase; nucleases which hydrolyze nucleic acid, e.g. ribonuclease, desoxyribonuclease; and amidases which hydrolyze amines, e.g. arginase, asparaginase, glutaminase and urease.

In the second group are redox enzymes which catalyze oxidation or reduction reactions. These include glucose oxidase, catalase, peroxidase, lipoxidase and cytochrome reductase.

The transferase enzymes of the third group transfer groups from one molecule to another. Typical of such enzymes are glutamicpyruvic transaminase, glutamicoxalacetic transaminase, transmethylase, phosphypyruvic transphosphorylase, and galactose-phosphateuridyltransferase.

The groups of enzymes mentioned can be insolubilized by establishing covalent (e.g. Axen, Porath, Ernback, Nature 214, 1302, 1967) or ionic linkages (Tosa, Mori, Fuse, Chibata, Biotech. Bioeng. 9, 603, 1967) between protein and support, or, entrapment of enzymes in cross-linked polymers (Mosbach and Mosbach, Acta Chem. Scand. 20, 2807, 1966). As carriers of enzymes, other proteins, e,g. collagen and molecules, polymers such as acrylic polymers and cellulose have been used. (Mosbach and Mosbach, Acta Chem. Scand. 20, 2807, 1966; Weetall and Weliky, Nature, 204, 896, 1964; Mitz and Summaria, Nature, 189, 576, 1961).

A coupling agent is used in order to provide a bond between the enzyme and the carrier. Depending on the available sites on the enzyme, or protein, molecule for bonding, suitable coupling agents are used to provide a bonding structure between the enzymes mentioned and the carrier. The coupling agent may be of the following types:

amide, sulfonamides, azo linkage, ether, ester, disulfide.

Principally, this is a two step reaction. The first step involves bonding the coupling agent to the carrier and the second step involves bonding the enzyme to the coupling agent-carrier combination.

Heparin has been chemically combined with polymers in insoluble complexes (Leininger, COoper, Falb, Grode, Nature, 152, 1625, 1966).

In accodance with the invention, blood is taken from an artery and caused to pass through a suitable apparatus containing a substance of the aforementioned category which presents a sufficiently wide active surface, and is then conducted back into a vein. As the blood passes over the active surface, the corresponding amino acid or acids or protein or proteins is or are selectively separated depending upon which enzyme or enzymes is or are used on the active surface. In this way it is possible during the time at disposal to lower the concentration of these substances in the blood quite considerably, thereby obtaining the desired therapeutic effect.

The resistance to flow in the apparatus is not greater than that which can be overcome by the pumping effect of the heart of a patient in good or relatively good health. In such instances where the heart is not capable alone of overcoming the resistance to flow through the apparatus, a conventional blood pump is connected in series with the apparatus. Alternatively, the active surface can be made to form an integrated portion of a blood pump of special design, wherewith the mentioned apparatus can be omitted. In the latter instance, the medically active substance is suitably fixed to the pump diaphragm.

Irrespective of design, the apparatus is provided with a manometer for controlling the blood pressure, and with a thermostatically controlled temperature regulating means for maintaining the temperature of the blood flowing therethrough essentially at body temperature.

It is desirable that the quantity of blood present in the apparatus is maintained as low as possible without the resistance to the flow of blood therethrough reaching an undesirable level. The surface to which the active substance is applied may take various forms. For instance the surface may be cylindrical or sheet-like in shape and the material may be fabric or of granular or fibrous structure or may comprise a cellular material of substantially open structure.

If the active surface is selected in the form of a hose having a wide diameter or a plurality of narrower hoses connected in parallel and throughpassed by the blood, each hose must be provided externally with an outer casing in the form of a plastic or metal tube or a hollow cylinder made of some appropriate material to prevent dialysis between the blood and the liquid in the temperature regulating means and to serve as a safety measure in the event of a fracture occurring in the hose positioned therewithin. Regarding the remainder of the aforementioned forms in which the active surface may be applied, the surface, and hence the active substance, is placed in the stream of blood, thus obviating the aforementioned safety measure. If the active substance is used in sheet form, it is expedient to arrange a plurality of parallel diaphragms or membranes in the form of planar sheets, concentric tubes, helically wound rolls, folded, undulating surfaces or combinations of these embodiments, to obtain a wide active surface within a small volume. The width of the gap between the active surfaces is adapted so that the resistance to the flow of the blood through the apparatus is relatively low. The membranes are affixed in their correct position by means of frameworks, supports, distance pieces or the like. When the active surfaces are made of fibrous or cellular material, suitable bodies are manufactured from the material and adapted to fit the space in the apparatus, where the selective separation process is to take place, e.g. cylinders or parallelepipeds. It should be understood that by the word membrane is meant any thin-walled structure, irrespective of shape.

The apparatus is used in the following manner. The active substance prepared with a hydrolytic enzyme or enzymes capable of separating the amino acid or protein which, according to diagnosis, should be removed from the blood, is placed in the apparatus in the form selected, e.g. in the form of a membrane, hoses or slugs, adapted to be accommodated in the apparatus. The temperature regulating means is then started and, subsequent to reaching the desired temperature, the input and ouput hoses of the apparatus are connected in a known manner to the artery and to a vein respectively in the arm of a patient.

Before connecting the hose to the vein, the manometer is checked to assure that the blood pressure of the patient will suffice to permit a sufficient quantity of blood to flow through the apparatus. It the apparatus is fitted with a blood pump and the pressure of the blood is not sufficient to overcome the resistance of the apparatus, the blood pump should be brought into operation. If the apparatus is not provided with a blood pump and the aforesaid conditions prevail, then the apparatus should be changed for one which is provided with a blood pump. During the process of the treatment, particularly when extending over long periods, it may be necessary to interrupt the process to replace the active surface for a new one, for instance when the original enzyme or enzymes have been completely or partially consumed. Subsequent to completion of the treatment, the connections to the blood vessels are removed and the patient bandaged.

Other objects and advantages of the present invention will be apparent from the following description, which is made with reference to the accompanying drawing.

The drawing illustrates a number of embodiments of the invention and

FIG. 1 shows the principle embodiment of the apparatus according to the invention;

FIG. 2 shows a cross section of a hose provided with a protective casing and intended for use in the selective separation process;

FIG. 3 shows in plan an embodiment of the active surface in the form of a planar sheet;

FIGS. 4-8 show examples of alternative ways in which the active sheet material may be folded or rolled;

Figure 5:
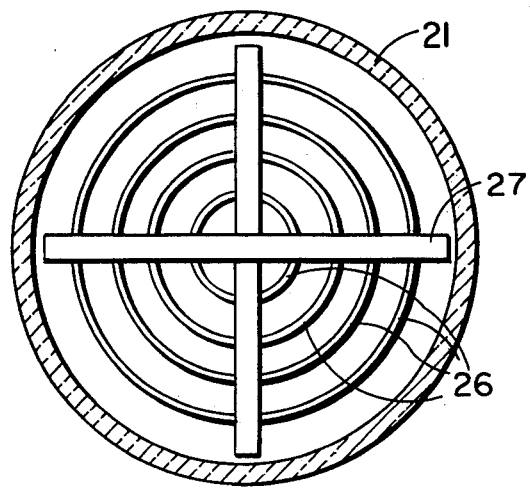

In the embodiment of FIG. 1 the blood is drained from an artery 1 through a delivery tube 2 to the input side 3 of a blood pump 4 of conventional design, which is provided with a by-pass line provided with valves 6, 7 and 8 If the heart of the patient is unable to pump a sufficient quantity of blood through the apparatus the blood pump is started, the valve 7 being held closed and the valves 6 and 8 open. If the heart of the patient is strong enough to move the blood through the apparatus, the blood pump 4 is by-passed by opening the valve 7 and closing the valves 6 and 8.

The blood is passed, via the hose 9, from the pressure side of the blood pump to the input side 11 of the selective separation arrangement 10. If it is known beforehand that the pumping capacity of the heart is sufficient, the blood pump 4 can alternatively be omitted completely, by connectng the hose 2 direct to the input side 11. This alternative has not been shown in the drawing.

The apparatus 10 for selectively separating amino acids and proteins comprises an outer container 12 having heat-insulated walls which contain a regulating means (not shown) which is controlled by a thermostat 13 and adapted to maintain the blood passing through the closed system at a constant temperature, the system being placed in the outer container 12. The closed system in the embodiment of FIG. 1 is in the form of a simple, open helix 14 which is connected with the input side 11 and the output side 15 of the apparatus. The helix 14 is shown cut away in FIG. 2, and comprises an outer protective casing 16, made of a plastic material, glass or metal, and an inner hose 17 of collagen, polymeric or copolymeric material, on which has been fixed an hydrolytic enzyme and heparin. In that instance when the outer protective casing 16 is not sufficiently self-supporting, the helix 14 is carried by a suitable support (not shown). When considered suitable, the helix 14 can be replaced by two or more hose-like, parallel-connected circuits of arbitrary form, having the cross section shown in FIG. 2 and connected to a distributor box and a collecting box. (This alternative has not been shown in the drawing). Positioned on the output side 15 of the apparatus 10 is a manometer 18, suitably graded in millimeters of Hg, and adapted to determine the pressure of the blood. The treated blood is returned from the output side 15 to a vein 20, through a return hose 19.

If the apparatus is used in the treatment of tumors, the growth of which requires normal concentration in the blood of the amino acid asparagin, the enzyme L-asparaginase is fixed to the active surface of the apparatus. Asparagine is degraded to aspartic acid and ammonia.

If the apparatus is employed in treating the disease galactosaemi, the enzyme galactose-1-phosphate uridyl transfarse is used on the active surface of the apparatus to remove galactose in the blood. Galactose is converted to glucose.

Figure 6:
Figure 7:
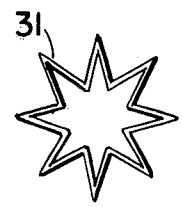
Figure 8:
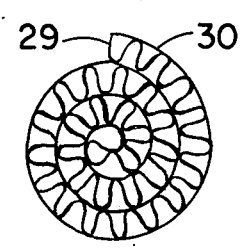

If it is desired to use collagen, polymeric or copolymeric materials, prepared in the aforesaid manner, in the form of a membrane, the helix 14 of FIG. 1 is changed for a closed chamber 21, e.g. in the shape of a parallelepiped or cylinder, and provided with an inlet 22 and an outlet 23, as shown in FIG. 3. The membrane is positioned in the interior of the chamber 21 in the form of one or more planar sheets 24 or folded sheets 25, as shown in FIG. 4. If the closed chamber 21 is of circular cross section, as shown in FIG. 5, the membrane 26 can be arranged in the form of a number of concentric tubes, fixed in appropriate spaced relationship by means of, for instance, holders 27. FIGS. 6, 7 and 8 show examples of other alternative embodiments of the membrane, in the form of respective spiral rolls 28, folded spirals 29 with flat support spiral 30 of the active membrane or of support material and starshaped folded membrane 31.

Figure 9:
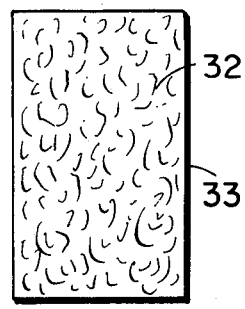
FIG. 9 shows a slug of fibrous material.

As illustrated in FIG. 9, permeable, filter-like bodies 33 of collagen, polymeric or copolymeric material in the form of fibrous material 32 can be manufactured to conform to the closed chamber 21 of FIGS. 3 and 5.

Figure 10:
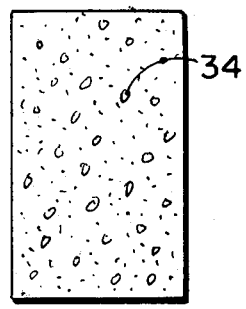
FIG. 10 shows a slug of cellular material.

As shown in FIG. 10, slugs made of collagen, polymeric or copolymeric material having substantially open cellular structure 34 can be manufactured, adapted to be accommodated in the closed chamber 21 of FIGS. 3 and 5.

Figure 11:
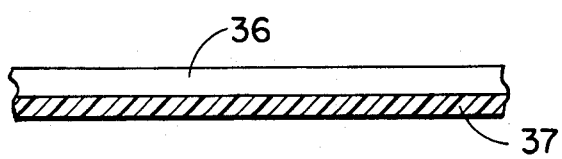
FIG. 11 shows a section through a membrane coated with active material and cooperating with a blood pump.

An alternative method of selectively separating amino acids and defined proteins in blood is to coat the internal surface completely or partially in a blood pump with collagen, polymeric or copolymeric material prepared in the aforesaid manner e.g. as shown in FIG. 11, where an active layer 37 of the aforementioned material is fixed to the pump diaphgragm 36.

It should be understood, however, that the apparatus and method for selectively separating amino acids and defined proteins from blood is not restricted to that which has been shown and described, and may be varied within the scope of the following claims.

What is claimed is:

1. An apparatus for selectively separating by enzymatic degradation amino acids and defined proteins from blood for therapeutic purposes, comprising walls forming a chamber, means positioned within said chamber forming at least one laterally closed and impervious passage therethrough, an inlet to said flow passage, an outlet from said flow passage a first tube for connecting said inlet to a human artery, a second tube for connecting said outlet to a human vein so that a closed system is provided for withdrawing blood from an artery, passing it through the flow passage in said chamber and returning it to a vein, a carrier material disposed within said flow passage for direct contact with the blood flowing therethrough and an enzyme suitable for separating one of an amino acid or a defined protein from blood fixed to said carrier material in an insolubilized manner for forming an active substance which effects a selective separation of at least one of the particular substances from the blood.

2. The apparatus of claim 1, characterized in that said carrier material is collagen, prepared with formaldehyde and phenol, to render it more durable and suitable for the intended purpose.

3. The apparatus of claim 1, characterized in that said carrier material is a polymeric material.

4. The apparatus of claim 1, characterized in that said carrier material is a copolymeric material.

5. The apparatus of claim 1, characterized in that said carrier material is in the form of a hose and is provided with an external sheath adapted to prevent dialysis and to serve as a safeguard in the event of a break in the inner hose.

6. The apparatus of claim 1, characterized in that said carrier material with its active forms a single member witin said flow passage.

7. The apparatus of claim 1, characterized in that said carrier material with its active surface is made up of a plurality of separate sections, and spacing members arranged to fix said sections of said carrier material in spaced relationship.

8. The apparatus of claim 6, characterized in that the active surface of said carrier material is flat.

9. The apparatus of claim 6, characterized in that the active surface of said carrier material presents a folded, undulating surface.

10. The apparatus of claim 6, characterized in that the active surface of said carrier material is tubular in shape.

11. The apparatus of claim 6, characterized in that the active surface of said carrier material is helical in shape.

12. The apparatus of claim 1, characterized in that said carrier material is a fibrous material and is positioned in said flow passage where the selective separation process takes place.

13. The apparatus of claim 1, characterized in that said carrier material is a substantially open cellular structure and is positioned in said flow passage where the selective separation process takes place.

14. The apparatus of claim 1, characterized by a blood pump arranged for pumping blood through the apparatus.

15. The apparatus of claim 14, characterized in that said carrier material including its active surface is incorporated into said pump in the path of the flow of blood therethrough.

16. The apparatus of claim 15, characterized in that said pump comprises a pump diaphragm formed by said carrier material with its active surface.

17. A method of selectively separating by enzymatic degradation amino acids and defined proteins from blood for therapeutic purpoes, comprising the steps of removing blood from a human artery, conveying the blood through a laterally closed impervious flow passage, directly contacting the blood within the flow passage with an active surface containing an enzyme insolubilized thereon and suitable for separating one of an amino acid or defined protein from the blood with the enzyme remaining in the active surface, and returning the blood to a human vein.

18. A method as set forth in claim 17, characterized therein by pumping the blood to be treated for passing it through the flow passage and returning it to the human vein.

* * * * *